(12) United States Patent
Shdema et al.

(10) Patent No.: US 10,642,793 B2
(45) Date of Patent: May 5, 2020

(54) METHOD AND SYSTEM FOR COMPRESSING GENOME SEQUENCES USING GRAPHIC PROCESSING UNITS

(71) Applicant: SQREAM TECHNOLOGIES LTD., Tel Aviv (IL)

(72) Inventors: Dotan Shdema, Netiv Ha'asara (IL); Raziel Shoshani, Rehovot (IL); Or Cohen, Tel Aviv (IL); Ori Netzer, Modi'in (IL)

(73) Assignee: SQREAM TECHNOLOGIES LTD, Tel Aviv (IL)

( * ) Notice: Subject to any disclaimer, the term of this patent is extended or adjusted under 35 U.S.C. 154(b) by 210 days.

(21) Appl. No.: 15/548,219

(22) PCT Filed: Feb. 2, 2016

(86) PCT No.: PCT/IL2016/050118
§ 371 (c)(1),
(2) Date: Aug. 2, 2017

(87) PCT Pub. No.: WO2016/125154
PCT Pub. Date: Aug. 11, 2016

(65) Prior Publication Data
US 2018/0011870 A1    Jan. 11, 2018

Related U.S. Application Data

(60) Provisional application No. 62/110,693, filed on Feb. 2, 2015.

(51) Int. Cl.
*G06F 17/00* (2019.01)
*G06F 16/174* (2019.01)
*G06F 16/242* (2019.01)
*G16B 50/00* (2019.01)
*G16B 30/00* (2019.01)
*G16B 40/00* (2019.01)

(52) U.S. Cl.
CPC ...... *G06F 16/1744* (2019.01); *G06F 16/2433* (2019.01); *G16B 30/00* (2019.02); *G16B 40/00* (2019.02); *G16B 50/00* (2019.02)

(58) Field of Classification Search
CPC . G06F 16/1744; G06F 16/2433; G06B 40/00; G06B 30/00
USPC .................................................. 707/600–899
See application file for complete search history.

(56) References Cited

U.S. PATENT DOCUMENTS

2013/0191351 A1*   7/2013   Baym .................... G16B 50/00
                                                              707/693
2014/0038836 A1    2/2014   Higgins et al.

* cited by examiner

*Primary Examiner* — Isaac M Woo
(74) *Attorney, Agent, or Firm* — Browdy and Neimark, P.L.L.C.

(57) ABSTRACT

The present invention provides a method for compressing genome sequences readers using GPU processing unit. The method comprising the steps of: identifying position of each given genome reader characters string in the sequence of a reference genome, determining alignment of each reader string within the reference genome, comparing each reader characters string to corresponding reference genome sequence based on determined alignment, filtering characters in each reader by GPU processor by eliminating similar characters and extracting only characters differences in association to their position in the genome sequence and recording filtered data of each reader in association to its alignment in genome reference at the genome compressed database.

9 Claims, 5 Drawing Sheets

METHOD AND SYSTEM FOR COMPRESSING GENOME SEQUENCES USING GRAPHIC PROCESSING UNITS

BACKGROUND

Technical Field

The present invention relates generally Method for compressing genome sequences and querying genome sequences database directly on GPU.

BRIEF SUMMARY

The present invention provides a method for compressing genome sequences readers using GPU processing unit. The method comprising the steps of: identifying position of each given genome reader characters string in the sequence of a reference genome, determining alignment of each reader string within the reference genome, comparing each reader characters string to corresponding reference genome sequence based on determined alignment, filtering characters in each reader by GPU processor by eliminating similar characters and extracting only characters differences in association to their position in the genome sequence and recording filtered data of each reader in association to its alignment in genome reference at the genome compressed database.

According to some embodiments of the present invention the method further comprising the step: on the fly clustering readers creating logical separation for storing data in chunks while maintaining the logical and physical storage boundaries as a metadata.

According to some embodiments of the present invention the clustering is performed by applying histograms.

According to some embodiments of the present invention the method further comprising the steps of: check a given SQL query parameters, determining readers strings to be retrieved based on query parameters, retrieve determined strings; and applying non-mutating query operators including at least one of join, filter or sort on multiple retrieved compressed readers based on reference gnome using the GPU multi-processing units.

According to some embodiments of the present invention the each GPU processing unit is assigned with at least one operator command applied on at least parameter or at least one reader.

The present invention provides a system for compressing genome sequences readers using GPU processing unit, said system comprised of: initial pre-possessing module for identifying position of each given genome reader characters string in the sequence of a reference genome; and determining alignment of each reader string within the reference genome, a compression module for comparing each reader characters string to corresponding reference genome sequence based on determined alignment, filtering characters in each reader by GPU processor by eliminating similar characters and extracting only characters differences in association to their position in the genome sequence and recording filtered data of each reader in association to its alignment in genome reference at the genome compressed database.

According to some embodiments of the present invention the initial pre-possessing is implemented in a CPU processor.

According to some embodiments of the present invention the initial pre-possessing is implemented in a GPU processor.

According to some embodiments of the present invention the initial pre-possessing module further preforms on the fly clustering readers creating logical separation for storing data in chunks while maintaining the logical and physical storage boundaries as a metadata.

According to some embodiments of the present invention the clustering is performed by applying histograms.

According to some embodiments of the present invention the system further comprising a data processing and analyzing module for preforming: checking a given SQL query parameters retrieve readers sequences based on query parameters and applying non-mutating query operators including at least one of join, filter or sort on multiple retrieved compressed readers based on reference gnome using the GPU multi-processing units.

These, additional, and/or other aspects and/or advantages of the present invention are: set forth in the detailed description which follows; possibly inferable from the detailed description; and/or learnable by practice of the present invention.

BRIEF DESCRIPTION OF THE DRAWINGS

The present invention will be more readily understood from the detailed description of embodiments thereof made in conjunction with the accompanying drawings of which.

DETAILED DESCRIPTION

Figure 1:
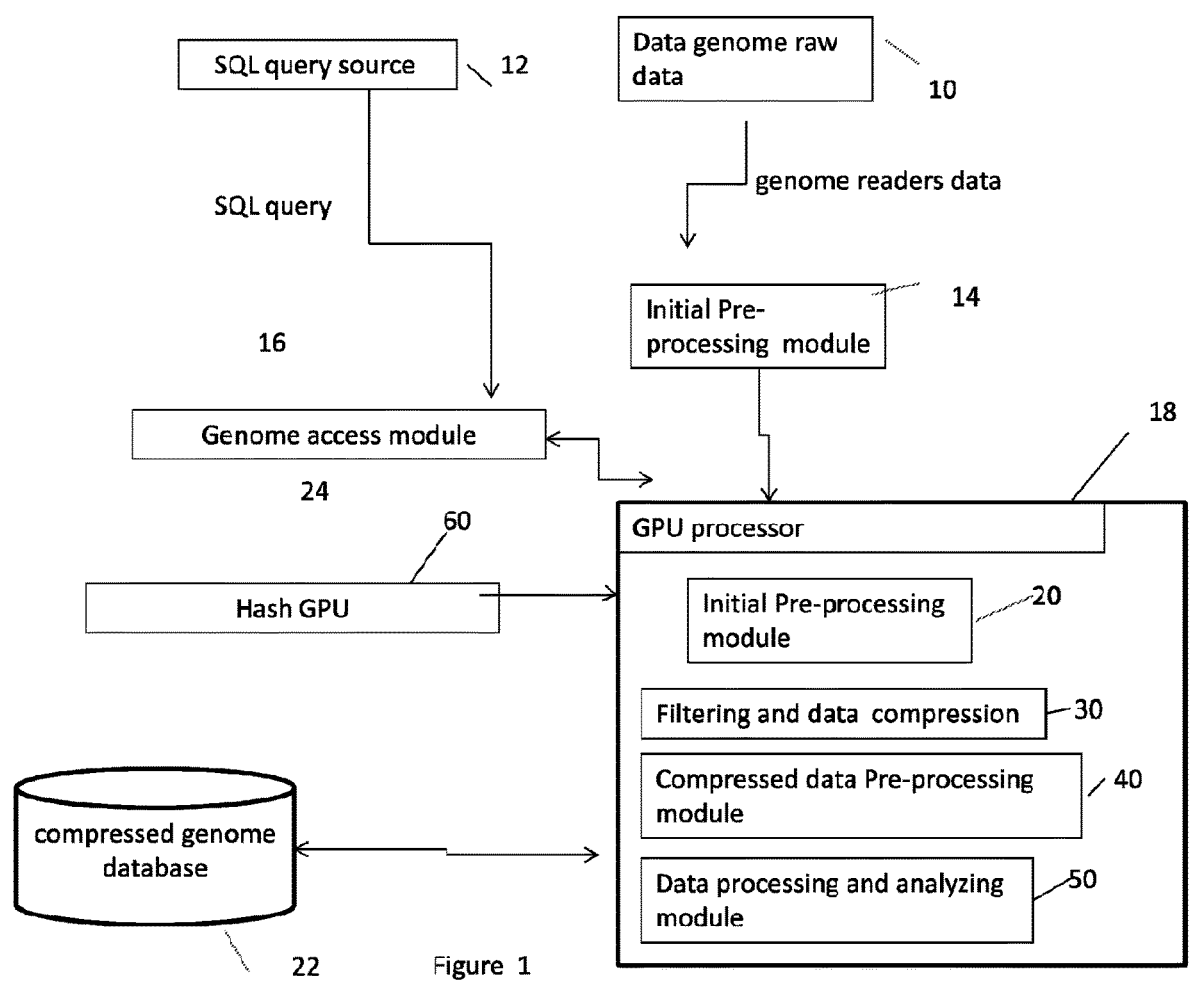
FIG. 1 illustrates a block diagram showing the entities and modules involved in in compressing genome sequences and preforming queries on compressed genome sequences database, according to some embodiments of the invention.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

The term "HWA (HardWare Accelerator):" as used herein in this application, is defined as any hardware that connected to main Central Processing Unit (CPU) through a Peripheral Component Interconnect (PCI) bus and encompasses a multiple computational cores inside. Example: GPGPUs (with 1000s of cores), Intel MICs (with 10s of cores). GPU or MIC or accelerators in this text are used interchangeably. In the context of present invention the GPU is being directly fed by data streamed from other device attached to PCI bus of the same host. This configuration could be used on single computer or multiple computers.

The term "SQL query" includes any database based query in any language on data that is streamed from storage or any other source.

The term "reference genome" as used herein in this application, is defined as a digital nucleic acid sequence database, assembled by scientists as a representative example of a species' set of genes. As they are often assembled from the sequencing of DNA from a number of donors, reference genomes do not accurately represent the set of genes of any single person The Read (or Reader) as used herein in this application, is defined a raw sequence that comes off a sequencing machine. A read may consist of multiple segments. For sequencing data, reads are indexed by the order in which they are sequenced.

The term "alignment" as used herein in this application, is defined is an alignment of a read to a single reference sequence by locating identical parts in different sequences FIG. 1 illustrates a block diagram showing the entities and modules involved in compressing genome sequences and preforming queries on compressed genome sequences database, according to some embodiments of the invention. Genome sequence readers 10, incoming from analysis of bio-samples, are processed by initial pre-possessing module 16 using CPU processor or initial pre-possessing module 14 using GPU processor. The pre-processed readers are compressed by the GPU processor 20. The GPU processor 20 includes a filtering and compressing unit for comparing each Genome sequence reader to a reference genome sequence using the Hash GPU 60. The compressed Genome sequence readers a pre-processed by the compressed data Pre-processing module 40 and recorded in the compressed genome database 22. Optionally, the compressing can be done by a single processing GPU which includes the data of the reference genome sequence. When a query request is received through Genome access module 16 from any query source 12, to be applied on the compressed genome database 22, the query is processed at the GPU processor by the Data processing and analyzing module 50.

Figure 2:
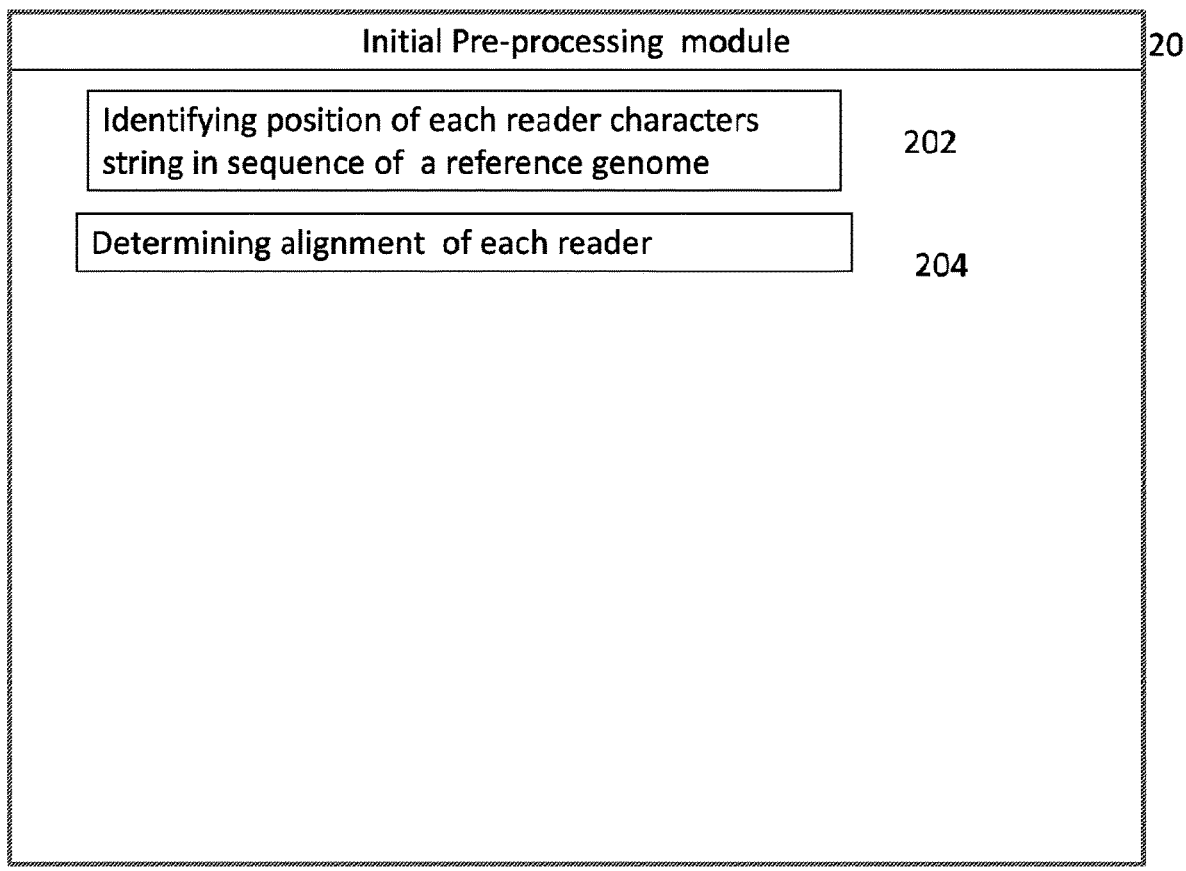
FIG. 2 is a flow diagram of Initial Pre-processing module, according to some embodiments of the invention
Figure 3:
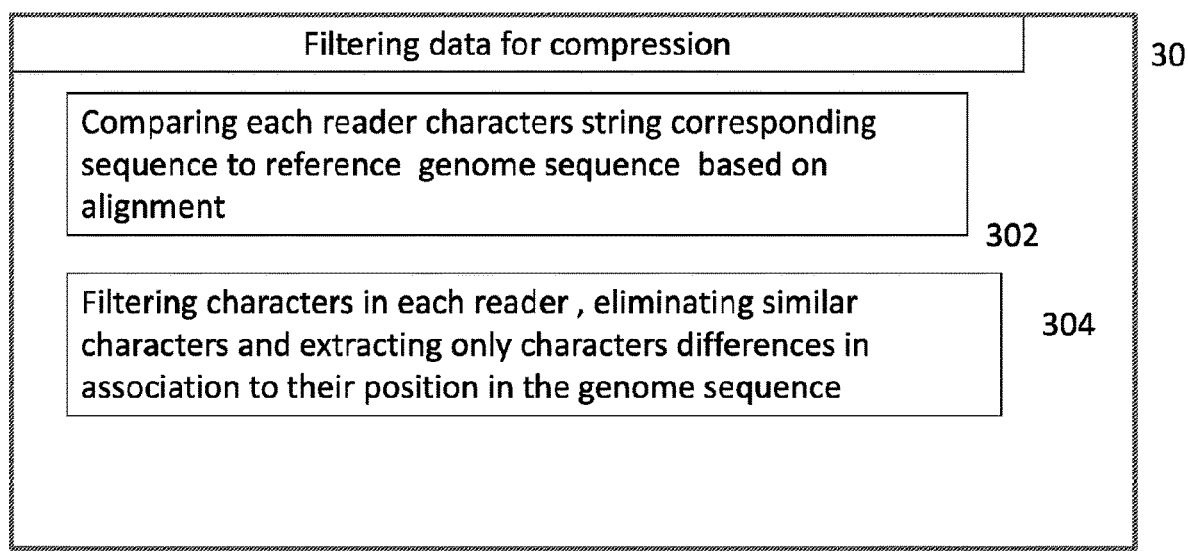
FIG. 3 is a flow diagram of filtering data for compression module, according to some embodiments of the invention.

FIG. 2 is a flow diagram of Initial Pre-processing module, according to some embodiments of the invention. This module preforms at least one of the following steps: identifying position of each reader in sequence of a reference genome (step 202) and determining alignment of each reader based on the identified position in relation to the reference genome (step 204), FIG. 3 is a flow diagram of filtering data for compression module, according to some embodiments of the invention. This module preforms at least one of the following steps: comparing each reader characters to the respective sequence in the reference genome based on determined alignment (step 302) and/or filtering characters in each reader (step 306) by eliminating similar characters and extracting only characters differences in association to their position in the reference genome sequence (step 304).

Figure 4:
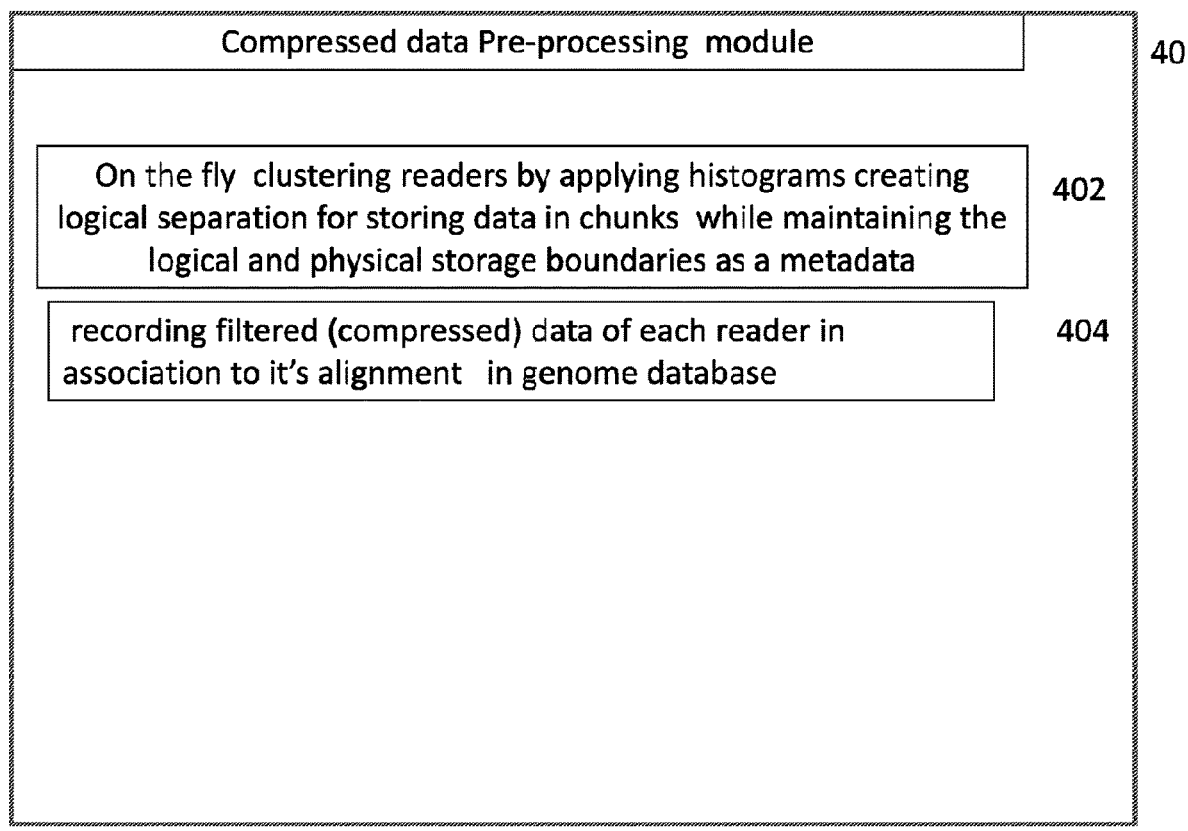
FIG. 4 is a flow diagram of Compressed data Pre-processing module, according to some embodiments of the invention

FIG. 4 is a flow diagram of compressed data Pre-processing module, according to some embodiments of the invention. This module preforms at least one of the following steps: On the fly clustering readers into logically separated groups for to be stored in plurality of data in chunks, the clustering maintains the logical and physical storage boundaries as a metadata (step 310) and recording filtered (compressed) data of each reader in association to its alignment position in genome database (step 12). According to some embodiments the clustering process is achieved by applying histograms.

According to some embodiments, the DNA readers clustering is implemented in the by applying the following process, apply direct DNA conversion: each DNA reader is represented as a vector of values from discrete final set $\{a,c,g,t\}$. In this process the vectors are padded with zeroes to equalize their length. This clustering supports performing SQL operators directly on the compressed readers.

Figure 5:
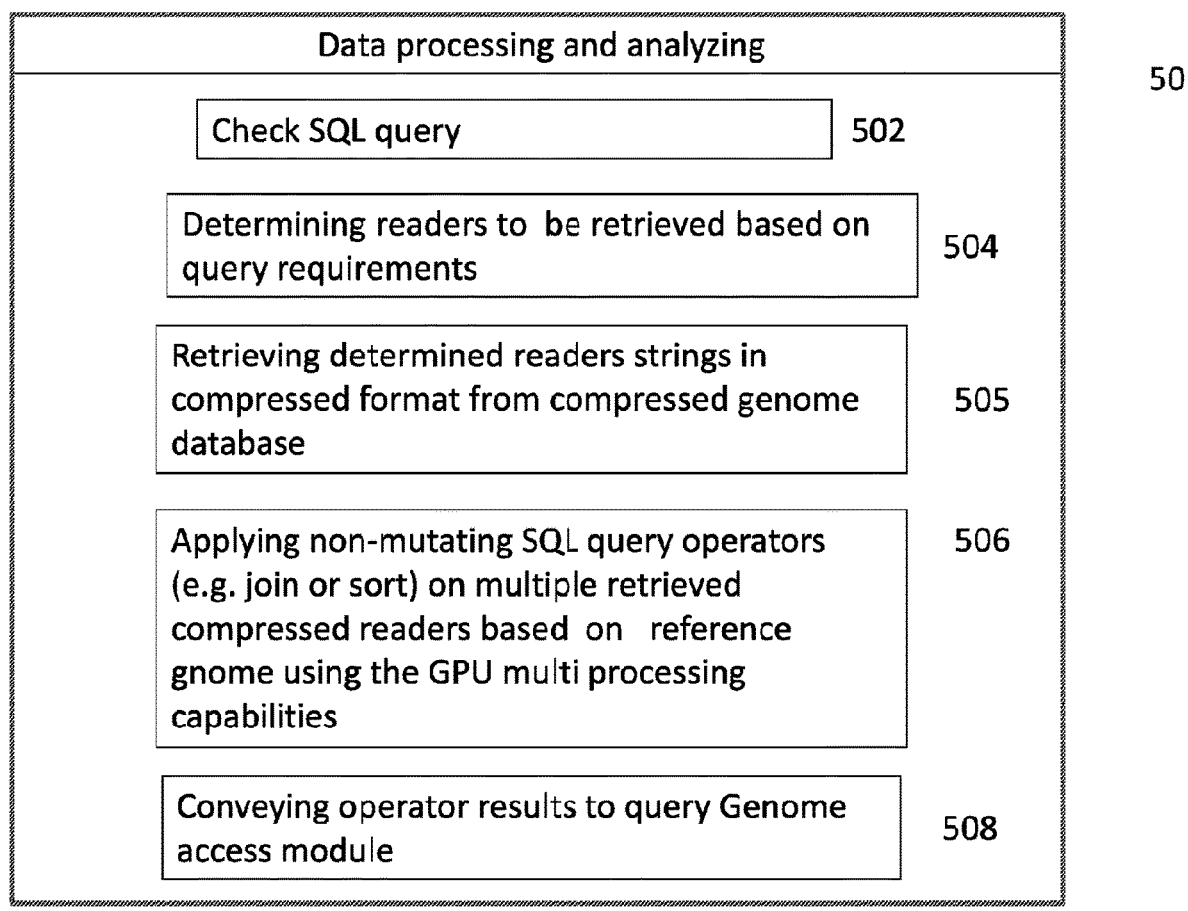
FIG. 5 is a flow diagram of the Data processing and analyzing module, according to some embodiments of the invention.

For Example: given the following DNA $\{aaacgggtt\}$ and $\{cccgtaagtc\}$ equal size vectors, we can calculate simple Euclidian distance by defining the following numeric values, e.g: A=1, C=2, G=3, T=4. This allows us to use known clustering algorithms such as k-means FIG. 5 is a flow diagram of the Data processing and analyzing module, according to some embodiments of the invention. This module preforms at least one of the following steps:

Check a given SQL query (step 410) identify query operators and parameters, for example, extract all genomes sequences having set of character X and Y;

determining readers to be retrieved based on query requirements as represented by their operators and parameters (step 420), in our example all reader which reader which are relevant for X and Y sequences are determined.

applying query operators (join, filter or sort) on multiple retrieved compressed readers based on reference gnome using the GPU multi-processing capabilities (step 430), for example each in joint query X and Y references are searched in all determined readers, the results include all readers in which both C and Y references were found. The query can be applied on the compressed readers, as the required properties for search are of the sequence part which are different form the reverence genome; and conveying operator results to query Genome access module (step 440).

The system of the present invention may include, according to certain embodiments of the invention, machine readable memory containing or otherwise storing a program of instructions which, when executed by the machine, implements some or all of the apparatus, methods, features and functionalities of the invention shown and described herein. Alternatively or in addition, the apparatus of the present invention may include, according to certain embodiments of the invention, a program as above which may be written in any conventional programming language, and optionally a machine for executing the program such as but not limited to a general purpose computer which may optionally be configured or activated in accordance with the teachings of the present invention. Any of the teachings incorporated herein may wherever suitable operate on signals representative of physical objects or substances.

Unless specifically stated otherwise, as apparent from the following discussions, it is appreciated that throughout the specification discussions, utilizing terms such as, "processing", "computing", "estimating", "selecting", "ranking", "grading", "calculating", "determining", "generating", "reassessing", "classifying", "generating", "producing", "stereo-matching", "registering", "detecting", "associating", "superimposing", "obtaining" or the like, refer to the action and/or processes of a computer or computing system, or processor or similar electronic computing device, that manipulate and/or transform data represented as physical, such as electronic, quantities within the computing system's registers and/or memories, into other data similarly represented as physical quantities within the computing system's memories, registers or other such information storage, transmission or display devices. The term "computer" should be broadly construed to cover any kind of electronic device with data processing capabilities, including, by way of non-limiting example, personal computers, servers, computing system, communication devices, processors (e.g. digital signal processor (DSP), microcontrollers, field programmable gate array (FPGA), application specific integrated circuit (ASIC), etc.) and other electronic computing devices.

The present invention may be described, merely for clarity, in terms of terminology specific to particular programming languages, operating systems, browsers, system versions, individual products, and the like. It will be appreciated that this terminology is intended to convey general principles of operation clearly and briefly, by way of example, and is not intended to limit the scope of the invention to any particular programming language, operating system, browser, system version, or individual product.

It is appreciated that software components of the present invention including programs and data may, if desired, be implemented in ROM (read only memory) form including CD-ROMs, EPROMs and EEPROMs, or may be stored in any other suitable typically non-transitory computer-readable medium such as but not limited to disks of various kinds, cards of various kinds and RAMs. Components described herein as software may, alternatively, be implemented wholly or partly in hardware, if desired, using conventional techniques. Conversely, components described herein as hardware may, alternatively, be implemented wholly or partly in software, if desired, using conventional techniques.

Included in the scope of the present invention, inter alia, are electromagnetic signals carrying computer-readable instructions for performing any or all of the steps of any of the methods shown and described herein, in any suitable order; machine-readable instructions for performing any or all of the steps of any of the methods shown and described herein, in any suitable order; program storage devices readable by machine, tangibly embodying a program of instructions executable by the machine to perform any or all of the steps of any of the methods shown and described herein, in any suitable order; a computer program product comprising a computer useable medium having computer readable program code, such as executable code, having embodied therein, and/or including computer readable program code for performing, any or all of the steps of any of the methods shown and described herein, in any suitable order; any technical effects brought about by any or all of the steps of any of the methods shown and described herein, when performed in any suitable order; any suitable apparatus or device or combination of such, programmed to perform, alone or in combination, any or all of the steps of any of the methods shown and described herein, in any suitable order; electronic devices each including a processor and a cooperating input device and/or output device and operative to perform in software any steps shown and described herein; information storage devices or physical records, such as disks or hard drives, causing a computer or other device to be configured so as to carry out any or all of the steps of any of the methods shown and described herein, in any suitable order; a program pre-stored e.g. in memory or on an information network such as the Internet, before or after being downloaded, which embodies any or all of the steps of any of the methods shown and described herein, in any suitable order, and the method of uploading or downloading such, and a system including server/s and/or client/s for using such; and hardware which performs any or all of the steps of any of the methods shown and described herein, in any suitable order, either alone or in conjunction with software. Any computer-readable or machine-readable media described herein is intended to include non-transitory computer- or machine-readable media.

Any computations or other forms of analysis described herein may be performed by a suitable computerized method. Any step described herein may be computer-implemented. The invention shown and described herein may include (a) using a computerized method to identify a solution to any of the problems or for any of the objectives described herein, the solution optionally include at least one of a decision, an action, a product, a service or any other information described herein that impacts, in a positive manner, a problem or objectives described herein; and (b) outputting the solution.

The scope of the present invention is not limited to structures and functions specifically described herein and is also intended to include devices which have the capacity to yield a structure, or perform a function, described herein, such that even though users of the device may not use the capacity, they are, if they so desire, able to modify the device to obtain the structure or function.

Features of the present invention which are described in the context of separate embodiments may also be provided in combination in a single embodiment.

For example, a system embodiment is intended to include a corresponding process embodiment. Also, each system embodiment is intended to include a server-centered "view" or client centered "view", or "view" from any other node of the system, of the entire functionality of the system, computer-readable medium, apparatus, including only those functionalities performed at that server or client or node.

What is claimed is:

1. A method for compressing and querying genome sequences readers database using GPU processing unit, said method comprising the steps of:
   identifying position of each given genome reader characters string in the sequence of a reference genome;
   determining alignment of each reader string within the reference genome;
   comparing each reader characters string to corresponding reference genome sequence based on determined alignment;
   filtering characters in each reader by GPU processor by eliminating similar characters and extracting only characters differences in association to position of the reader in the genome sequence;
   recording filtered data of each reader in association to said reader's alignment in the genome reference at the genome compressed database;
   checking a given SQL query parameters;
   determining readers strings to be retrieved based on query parameters;
   retrieving determined strings; and
   applying non-mutating query operators including join, filter and sort on multiple retrieved compressed readers based on reference genome using the OPU multi-processing unit.

2. The method of claim 1 further comprising the step: on the fly clustering readers creating logical separation for storing data in chunks while maintaining the logical and physical storage boundaries as a metadata.

3. The method of claim 1 wherein the clustering is performed by applying histograms.

4. The method of claim 1 wherein the GPU processing unit is assigned with at least one operator command applied on at least parameter or at least one reader.

5. A system for compressing genome sequences readers using GPU processing unit, said system comprised of:
- initial pre-possessing module for identifying position of each given genome reader characters string in the sequence of a reference genome; and determining alignment of each reader string within the reference genome;
- a compression module for comparing each reader characters string to corresponding reference genome sequence based on determined alignment, filtering characters in each reader by GPU processor by eliminating similar characters and extracting only characters differences in association to position of the reader in the genome sequence and recording filtered data of each reader in association to said reader's alignment in the genome reference at the genome compressed database;
- a data processing and analyzing module for preforming: checking a given SQL query parameters, retrieving readers sequences, based on query parameters, and applying non-mutating query operators including join, filter and sort on multiple retrieved compressed readers based on reference genome using the GPU multi-processing unit.

6. The system of claim 5 wherein the initial pre-possessing is implemented in a CPU processor.

7. The system of claim 5 wherein the initial pre-possessing is implemented in a GPU processor.

8. The system of claim 5 wherein initial pre-possessing module further preforms on the fly clustering readers creating logical separation for storing data in chunks while maintaining the logical and physical storage boundaries as a metadata.

9. The system of claim 8 wherein the clustering is performed by applying histograms.

\* \* \* \* \*